(12) United States Patent
Sharrow (10) Patent No.: US 8,167,821 B2
(45) Date of Patent: May 1, 2012

(54) MULTIPLE DIAMETER GUIDEWIRE

(75) Inventor: James S. Sharrow, Bloomington, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2711 days.

(21) Appl. No.: 10/375,634

(22) Filed: Feb. 26, 2003

(65) Prior Publication Data

US 2004/0167440 A1 Aug. 26, 2004

(51) Int. Cl.
*A61B 5/00* (2006.01)
*A61M 25/00* (2006.01)

(52) U.S. Cl. ........ 600/585; 600/433; 600/434; 600/435; 604/164.13

(58) Field of Classification Search .................. 600/585, 600/433–435; 604/164.13
See application file for complete search history.

(56) References Cited

U.S. PATENT DOCUMENTS

| | | | |
|---|---|---|---|
| 4,505,767 A | 3/1985 | Quin | |
| 4,512,338 A | 4/1985 | Balko et al. | |
| 4,538,622 A | 9/1985 | Samson et al. | |
| 4,554,929 A | 11/1985 | Samson et al. | |
| 4,601,283 A | 7/1986 | Chikama | |
| 4,631,094 A | 12/1986 | Simpson et al. | |
| 4,634,477 A | 1/1987 | Sugimoto et al. | |
| 4,657,822 A | 4/1987 | Goldstein | |
| 4,665,906 A | 5/1987 | Jervis | |
| 4,763,647 A | 8/1988 | Gambale | |
| 4,770,725 A | 9/1988 | Simpson et al. | |
| 4,811,743 A | 3/1989 | Stevens | |
| 4,846,186 A | 7/1989 | Box et al. | |
| 4,922,924 A | 5/1990 | Gambale et al. | |
| 4,925,445 A | 5/1990 | Sakamoto et al. | |
| 5,059,183 A | 10/1991 | Semrad | |
| 5,063,935 A | 11/1991 | Gambale | |
| 5,067,489 A | 11/1991 | Lind | |
| RE33,911 E | 5/1992 | Samson et al. | |
| 5,144,959 A | 9/1992 | Gambale et al. | |
| 5,147,317 A | 9/1992 | Shank et al. | |
| 5,174,302 A * | 12/1992 | Palmer | 600/585 |
| 5,192,295 A | 3/1993 | Danforth et al. | |
| 5,228,453 A | 7/1993 | Sepetka | |
| 5,238,004 A | 8/1993 | Sahatjian et al. | |
| 5,246,009 A | 9/1993 | Adams | |
| 5,253,653 A | 10/1993 | Daigle et al. | |
| 5,303,714 A | 4/1994 | Abele et al. | |

(Continued)

FOREIGN PATENT DOCUMENTS

WO 9208510 5/1992

(Continued)

OTHER PUBLICATIONS http://training.seer.cancer.gov/ss_module14_melanoma/unit02_sec01_anatomy.html.*

*Primary Examiner* — Rene Towa
(74) *Attorney, Agent, or Firm* — Seager, Tufte & Wickhem, LLC (57) ABSTRACT

A guidewire can include a shaft or core wire that has a distal section configured for access to a vascular treatment site and a proximal section configured for intervention at a vascular treatment site. At least a portion of the distal section of the shaft or core wire can have a diameter that is greater than a diameter of the proximal section.

18 Claims, 7 Drawing Sheets

U.S. PATENT DOCUMENTS

| | | | |
|---|---|---|---|
| 5,341,818 A * | 8/1994 | Abrams et al. | 600/585 |
| 5,345,945 A | 9/1994 | Hodgson et al. | |
| 5,363,847 A | 11/1994 | Viera | |
| 5,385,152 A * | 1/1995 | Abele et al. | 600/585 |
| 5,409,015 A | 4/1995 | Palermo | |
| 5,411,033 A | 5/1995 | Viera | |
| 5,429,139 A | 7/1995 | Sauter | |
| 5,465,733 A | 11/1995 | Hinohara et al. | |
| 5,479,938 A | 1/1996 | Weier | |
| 5,488,959 A | 2/1996 | Ales | |
| 5,497,783 A | 3/1996 | Urick et al. | |
| 5,498,250 A | 3/1996 | Prather | |
| 5,527,298 A | 6/1996 | Vance et al. | |
| 5,546,948 A | 8/1996 | Hamm et al. | |
| 5,606,979 A | 3/1997 | Hodgson | |
| 5,636,642 A | 6/1997 | Palermo | |
| 5,640,970 A | 6/1997 | Arenas | |
| 5,666,969 A | 9/1997 | Urick et al. | |
| 5,695,111 A * | 12/1997 | Nanis et al. | 228/206 |
| 5,706,826 A | 1/1998 | Schwager | |
| 5,720,300 A | 2/1998 | Fagan et al. | |
| 5,724,989 A * | 3/1998 | Dobson | 600/585 |
| 5,749,837 A | 5/1998 | Palermo et al. | |
| 5,769,796 A | 6/1998 | Palermo et al. | |
| 5,772,609 A | 6/1998 | Nguyen et al. | |
| 5,782,741 A | 7/1998 | Bradshaw et al. | |
| 5,788,654 A | 8/1998 | Schwager | |
| 5,797,856 A | 8/1998 | Frisbie et al. | |
| 5,797,857 A | 8/1998 | Obitsu | |
| 5,827,201 A | 10/1998 | Samson et al. | |
| 5,830,155 A * | 11/1998 | Frechette et al. | 600/585 |
| 5,833,631 A | 11/1998 | Nguyen | |
| 5,876,356 A | 3/1999 | Viera et al. | |
| 5,931,819 A | 8/1999 | Fariabi | |
| 5,957,903 A * | 9/1999 | Mirzaee et al. | 604/524 |
| 6,019,736 A | 2/2000 | Avellanet et al. | |
| 6,039,699 A | 3/2000 | Viera | |
| 6,068,623 A | 5/2000 | Zadno-Azizi et al. | |
| 6,132,389 A | 10/2000 | Cornish et al. | |
| 6,139,510 A | 10/2000 | Palermo | |
| 6,139,511 A | 10/2000 | Huter et al. | |
| 6,142,975 A | 11/2000 | Jalisi et al. | |
| 6,165,140 A | 12/2000 | Ferrera | |
| 6,165,292 A | 12/2000 | Abrams et al. | |
| 6,168,570 B1 | 1/2001 | Ferrera | |
| 6,168,571 B1 | 1/2001 | Solar et al. | |
| 6,190,332 B1 | 2/2001 | Muni et al. | |
| 6,217,567 B1 | 4/2001 | Zadno-Azizi et al. | |
| 6,234,981 B1 | 5/2001 | Howland | |
| 6,241,690 B1 | 6/2001 | Burkett et al. | |
| 6,254,550 B1 | 7/2001 | McNamara et al. | |
| 6,287,292 B1 | 9/2001 | Fariabi | |
| 6,296,622 B1 | 10/2001 | Kurz et al. | |
| 6,306,105 B1 | 10/2001 | Rooney et al. | |
| 6,348,041 B1 | 2/2002 | Klint | |
| 6,355,016 B1 | 3/2002 | Bagaoisan et al. | |
| 6,375,629 B1 | 4/2002 | Muni et al. | |
| 6,383,146 B1 | 5/2002 | Klint | |
| 6,387,060 B1 | 5/2002 | Jalisi | |
| 6,390,993 B1 | 5/2002 | Cornish et al. | |
| 6,428,512 B1 | 8/2002 | Anderson et al. | |
| 6,432,066 B1 | 8/2002 | Ferrera | |
| 6,475,169 B2 | 11/2002 | Ferrera | |
| 6,478,773 B1 | 11/2002 | Gandhi et al. | |
| 6,482,166 B1 | 11/2002 | Fariabi | |
| 6,488,637 B1 | 12/2002 | Eder et al. | |
| 6,491,648 B1 | 12/2002 | Cornish et al. | |
| 6,494,894 B2 | 12/2002 | Mirarchi | |
| 6,500,149 B2 | 12/2002 | Gandhi et al. | |
| 6,508,803 B1 | 1/2003 | Horikawa et al. | |
| 6,524,301 B1 | 2/2003 | Wilson et al. | |
| 2003/0069520 A1 | 4/2003 | Skujins et al. | |
| 2003/0069521 A1 | 4/2003 | Reynolds et al. | |

FOREIGN PATENT DOCUMENTS

| | | |
|---|---|---|
| WO | 9413350 | 6/1994 |

* cited by examiner

MULTIPLE DIAMETER GUIDEWIRE

TECHNICAL FIELD

The invention pertains generally to elongate medical devices such as guidewires.

BACKGROUND

A wide variety of elongate medical devices such as guidewires have been developed for use in conjunction with devices such as catheters to facilitate navigation through the anatomy of a patient. Guidewires can be used to access and navigate to a desired treatment site within the anatomy of a patient. Guidewires are often used as a guide for other devices that can be fed over the guidewire to the treatment site. Guidewires sometimes include a wider diameter proximal portion that is designed for relatively greater stiffness to enhance pushability and torqueability, and a distal portion that is designed for relatively greater lateral flexibility to enhance trackability and steerability. However, in at least some cases, the wider outer diameter proximal portion of the wire, which provides the desired, or even required stiffness characteristics for the particular procedure being performed, can interfere with the guidewires ability to function as guide for other devices. The larger outer diameter of the proximal portion may interfere with the feeding of some other devices over the wire. As such, during some procedures, it is often necessary to exchange one wire having the desired stiffness characteristics for another wire having the desired diameter for use as a guide for a particular device. Such exchanges are often undesirable. A number of different guidewire structures and assemblies are known, each having certain advantages and disadvantages. However, there is an ongoing need to provide alternative guidewire structures and assemblies.

SUMMARY

The invention provides several alternative designs, materials, and methods of manufacturing alternative guidewire structures, assemblies, and the like. Some embodiments relate to a guidewire including an elongate shaft that has a distal section that is adapted or configured for navigating within the vasculature to a treatment site, and a proximal section that is adapted or configured for use as a platform or guide for another device. In some embodiments, the distal section includes a region having an outside diameter that is greater than an outside diameter of the proximal section, and can have a length configured to extend from a first position adjacent a target site in the anatomy to a second position outside the patient. Additionally, the proximal section can have a length configured to extend from the first position adjacent the target site in the anatomy to the second position outside the patient. In some embodiments, the guidewire can include a core wire having a distal section and a proximal section, wherein the distal section of the core wire includes a portion having an outside diameter that is greater than an outside diameter of the proximal section of the core wire, and the distal section of the core wire has a length configured to extend from a first position adjacent a target site in the anatomy to a second position outside the patient. Additionally, some other embodiments relate to methods of making guidewires, while some other embodiments relate to a method of navigating or accessing a treatment site within an anatomy of a patient.

The above summary of some example embodiments is not intended to describe each disclosed embodiment or every implementation of the present invention. The Figures, and Detailed Description which follow more particularly exemplify these embodiments.

BRIEF DESCRIPTION OF THE FIGURES

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following terms, these meanings shall be applied, unless a different meaning is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention. For example, although discussed with specific reference to guidewires in the particular embodiments described below, the invention may be applicable to a variety of medical devices that are adapted to be advanced into the anatomy of a patient through an opening or lumen, and includes a portion that can act as a guide or platform for another medical device which can be disposed thereon or advanced thereover. Such devices can be considered as functioning as a guidewire. Additionally, although discussed with specific reference to guiding members for use in intravascular procedures, the invention may be applicable to a variety of other procedures, for example, endoscopic, laproscopic, spinal, or cranial procedures, and the like.

In at least some embodiments, the invention disclosed herein relates to a guidewire that can be used as both a navigational tool, and as a device to aid in intervention at a treatment site. For example, the guidewire can include a distal section that is adapted or configured for navigating within the vasculature to a treatment site, and a proximal section that is adapted or configured for use as a platform or guide for another device.

Figure 1:
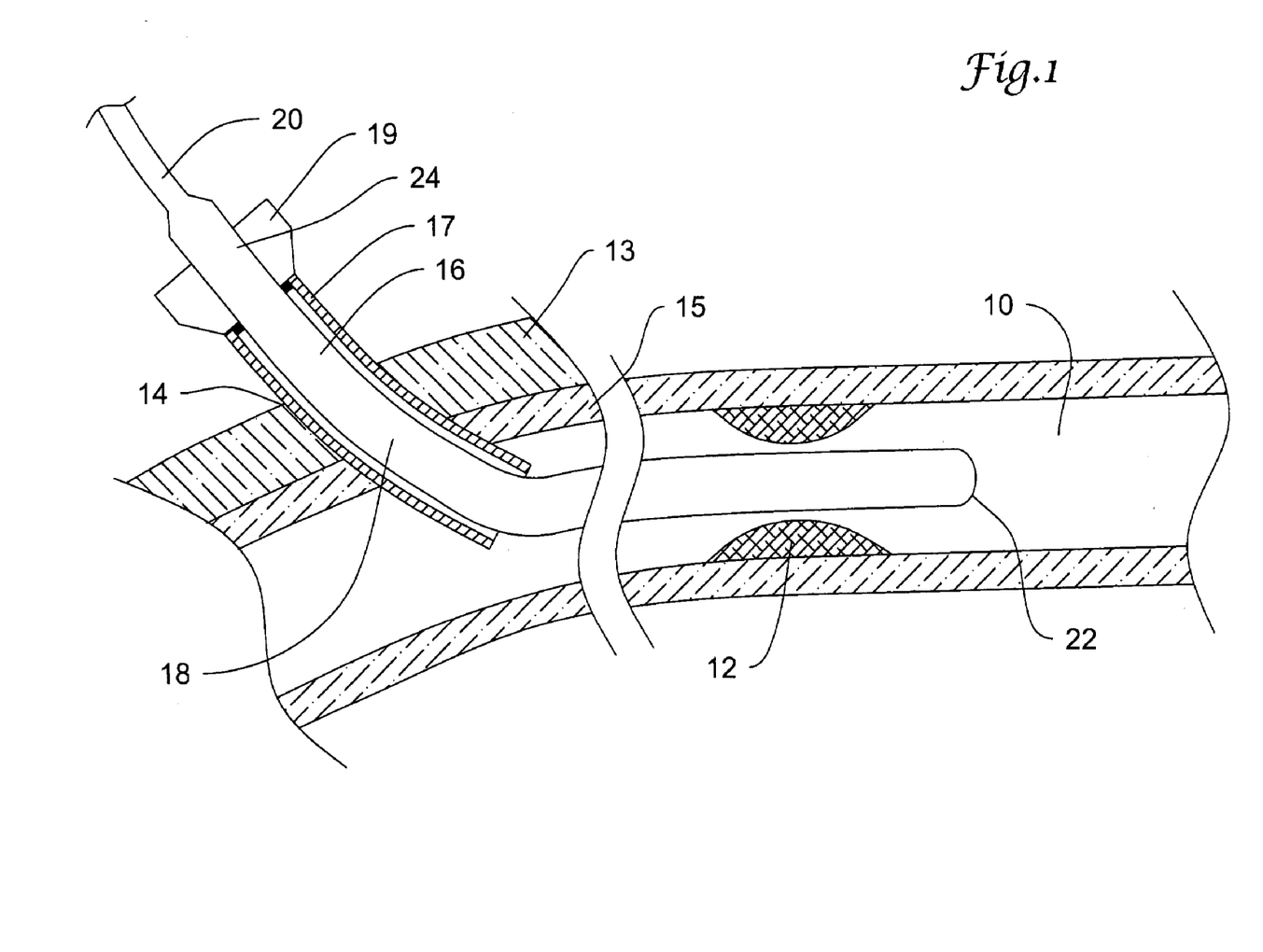
FIG. 1 is a diagrammatical view of a guidewire in accordance with an embodiment of the invention, showing the guidewire inserted such that a distal end of the distal portion is proximate a lesion while the proximal end of the distal portion remains proximal of a vascular access point.
Figure 2:
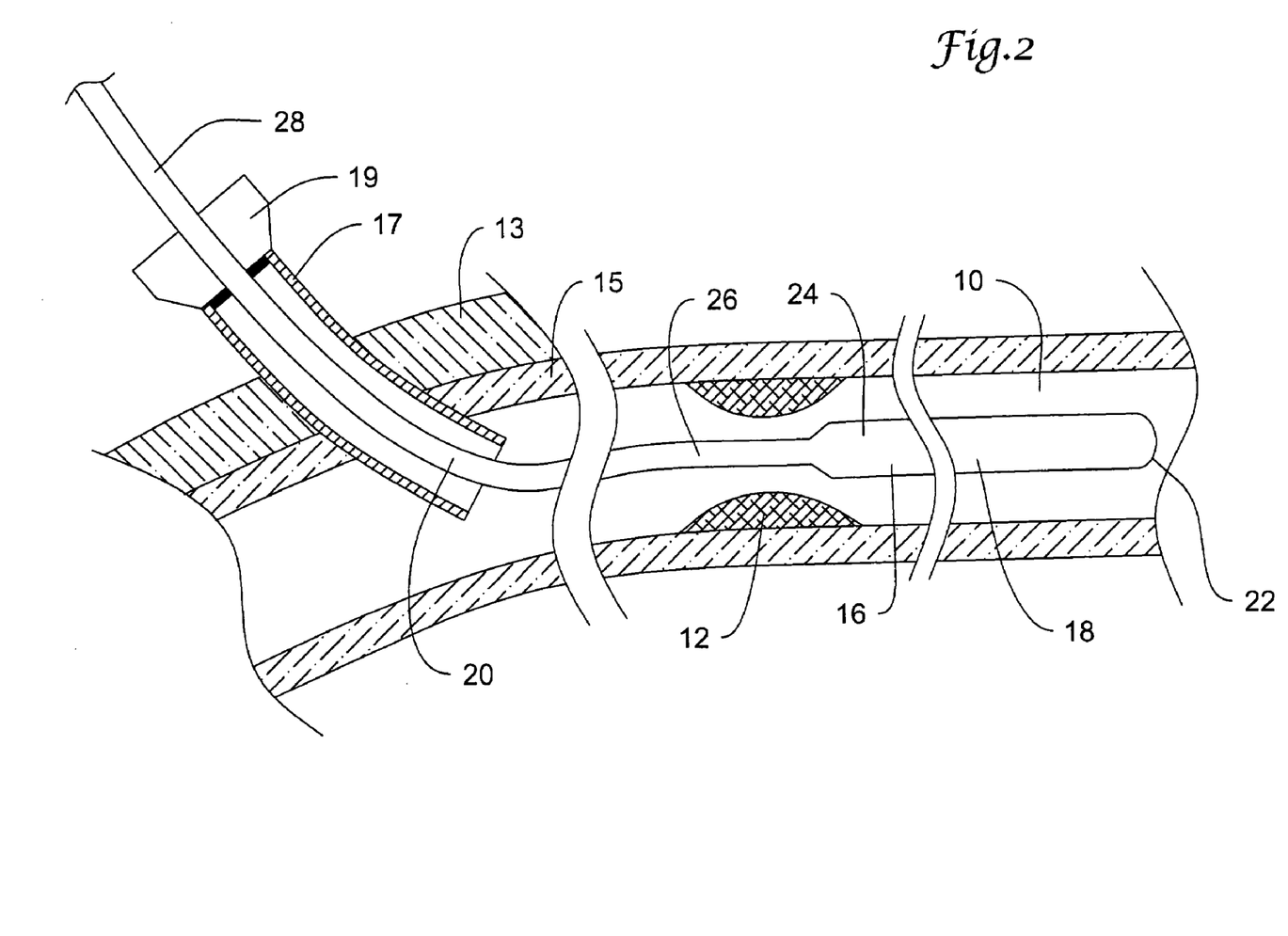
FIG. 2 is a diagrammatical view of the guidewire of FIG. 1, showing the guidewire advanced distally to a position where the proximal end of the distal portion is proximate or just past the lesion, and a proximal end of the proximal portion remains proximal of the vascular access point.
Figure 2A:
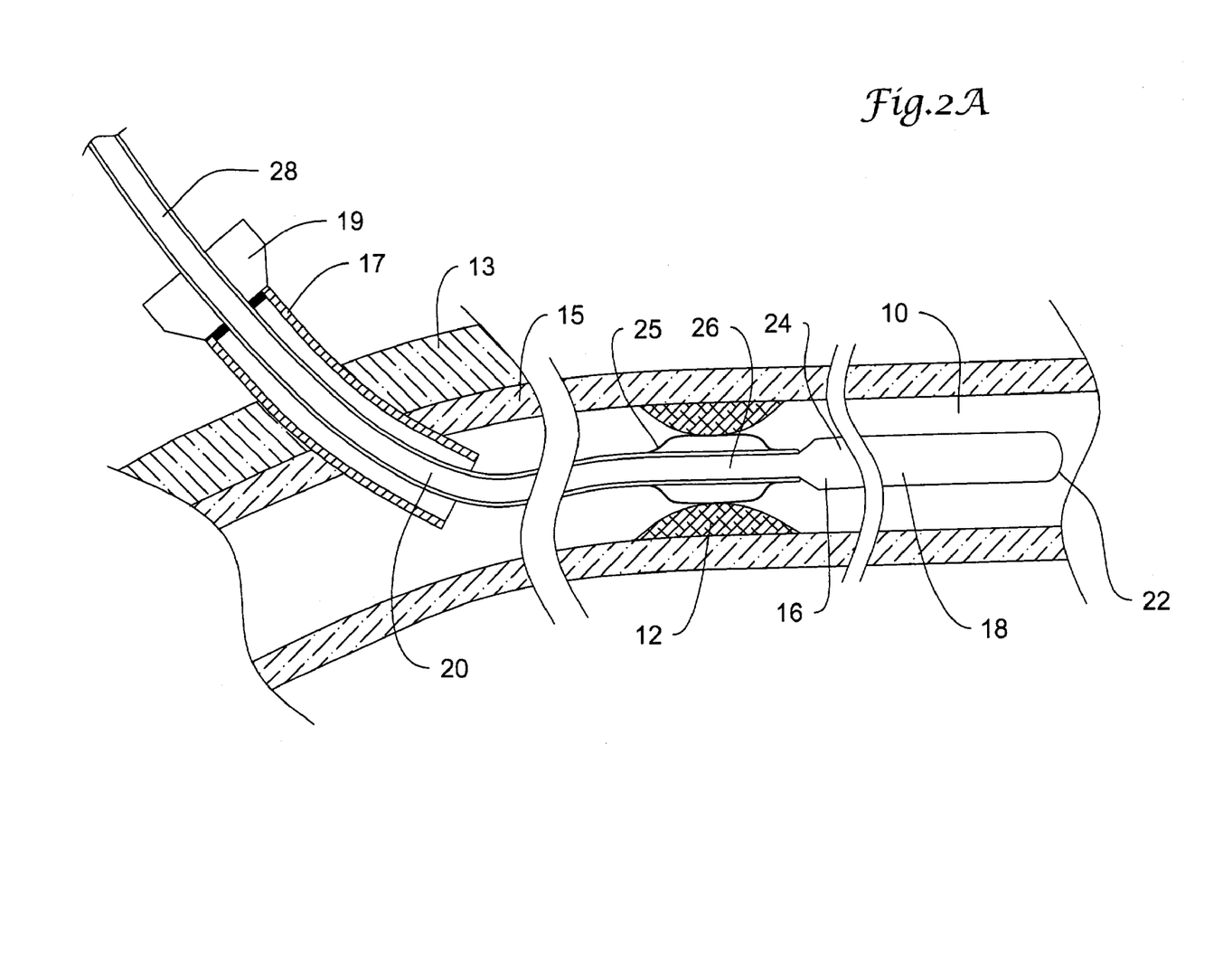
FIG. 2A is a diagrammatical view of the guidewire of FIG. 2, showing a balloon catheter advanced over the proximal portion of the guidewire to a position adjacent the lesion.

Refer now to FIGS. 1-2A, which are diagrammatic representations of a guidewire 16 that is partially disposed in a portion 10 of a patient's vasculature including a treatment site 12, such as an occlusion, lesion or the like. The guidewire extends into the vasculature of a patient through a vascular access point 14. The vascular access point 14 can represent any suitable means to reach the interior of a patient's vasculature, such as an introducer sheath, a guide catheter, or the like. In some embodiments, as illustrated, an introducer sheath 17 having a port 19 at its distal end can be used which extends through a patient's intervening tissue 13 and through a vessel wall 15 to reach the vessel lumen 10, as is generally known. In some embodiments, the port 19 can include any structure that permits access to an interior of the introducer sheath 17. In some embodiments, the port 19 can include a fitting or valve such as a hemostasis fitting or valve.

The guidewire 16 includes at least two distinct sections—a distal section 18 and a proximal section 20. The distal section 18 can be considered as being adapted or configured for gaining access to and/or navigating within the vasculature to a treatment site and/or crossing the treatment site 12. The proximal section 20 can be considered as being adapted or configured to act as an aid for intervention using another device at the treatment site 12. For example, the proximal section 20 can be adapted or configured to act as a guide or platform for another medical device which can be disposed thereon or advanced thereover.

The distal section 18 includes a distal portion 22 and a proximal portion 24. The distal section 18 can include at least a portion thereof, such as proximal portion 24, that defines a relatively larger outer diameter in relation to the outer diameter of at least a portion of the proximal section 20. The relatively large outer diameter of at least a portion of the distal section 18 can be provided to enhance certain navigational characteristics, such as pushability and torqueability. In the embodiment shown, the entire distal section 18 includes a constant, relatively larger outer diameter in relation to the outer diameter of the proximal section 20. However, in some embodiments, the distal section 18 could also include a distal portion thereof that is adapted to be more flexible to allow for navigational characteristics such as trackability and steerability. For example, the distal section 18 could include a distally tapering outer diameter, a distally tapering core wire, or could include or be made of different materials to enhance flexibility characteristics near the distal portion 22, as will be discussed in more detail below. However, at least a significant portion of the length of the distal section 18 includes an outer diameter that is larger than the outer diameter of the proximal section 20. For example, in some embodiments, in the range of about 20% or more, or about 40% or more, or about 60% or more of the length of the distal section 18 includes an outer diameter that is larger than the outer diameter of the proximal section 20.

The distal section 18 is of such a length that at least a part of the proximal portion 24 thereof can extend outside of the patients body for manipulation by an operator when the distal portion 22 thereof is adjacent the treatment site 12. As such, the distal section 18 can be used to navigate the entire length of the vasculature between the vascular access point 14 and the treatment site 12.

The proximal section 20 can have an outer diameter that is reduced in size relative to the outer diameter of at least a portion of the distal section 18. For example, proximal section 20 can have an outer diameter that is smaller than the outer diameter of the proximal portion 24 of the distal section 18. The proximal section 20 includes a distal portion 26 and a proximal portion 28 (as seen in FIG. 2). The distal portion 26 of the proximal section 20 can be connected to the proximal portion 24 of the distal section 18, for example, in a tapering junction wherein the smaller outer diameter of the distal portion 26 of the proximal section 20 tapers up to the larger outer diameter of the proximal portion 24 of the distal section 18. The proximal section 18 is of such a length that at least a part of the proximal portion 28 can extend outside of the patients body for manipulation by an operator when the distal portion 26 is adjacent the treatment site 12. As such, the proximal section 18, when extended into the vasculature, can be used as a guide for other devices for the entire length of the vasculature between the vascular access point 14 and the treatment site 12.

In use, the distal portion 18 of the guidewire 16 could be used by an operator to access a portion of the vascular anatomy, to navigate and steer the guidewire 16, make contact with, and/or cross the treatment site 12, as shown in FIG. 1. In FIG. 1, the guidewire 16 is positioned such that a distal portion 22 of the distal section 18 is proximate to or just distal of the treatment site 12. Because the distal section 18 has a length that permits the distal end 22 of the distal section 18 to reach or pass the occlusion 12 while a proximal end 24 of the distal section 18 remains outside of the anatomy proximate the vascular access point 14, an operator can manipulate the distal section 18 during the initial navigation to the treatment site 12, while the proximal section 18 of the guidewire 16 remains outside of the vasculature.

Thereafter, the distal section 18 can be pushed distally beyond the treatment site 12 within the vasculature as the distal portion 26 of the proximal section 20 is advanced into the vasculature, as shown in FIG. 2. In some embodiments, it is advantageous for the vasculature distal of the treatment site 12 to be adequate to accept the distal section 18. The distal portion 26 of the proximal section 20 is positioned adjacent to or just distal to the treatment site 12, while at least a part of the proximal portion 28 of the proximal section 20 remains proximal of the vascular access point 14. With the guidewire 16 positioned as shown in FIG. 2, any of a variety of interventional devices such as balloon catheters, stent delivery catheters, cutting catheters, infusion devices, and the like can be administered to the treatment site 12 by passing the interventional device over the proximal portion 28 of the proximal section 20, and advancing them to the treatment site 12 over the proximal section 20. For example, FIG. 2A shows a balloon catheter 25 advanced over the proximal section 20 of the guidewire 16 to a position adjacent to the treatment site 12.

As can be seen from the above discussion, both the proximal section 20 and the distal section 18 have a length that is at least as great, and in come cases, somewhat greater than the distance between the treatment site 12 and the vascular access point 14. Therefore, both the proximal section 20 and the distal section 18 individually make up a significant portion of the total length of the guidewire 16. In some embodiments, the proximal section 20 can have a length that is greater than the length of the distal section 18, due at least in some cases to the fact that the distal section 18 will need to be advanced distally beyond the treatment site in the vasculature, and additional length may therefore not be desired. In some embodiments, the distal section 18 can make up in the range of about 10% to about 50%, or in the range of about 30% to about 50% of the total length of the guidewire, while the proximal section 20 would make up the remainder.

In some example embodiments, the distal section 18 can have a maximum outer diameter that is in the range of about 0.025 to 0.040 inches and a length that is in the range of about 6 to 18 inches. The proximal section 20 can have an outer diameter that is in the range of about 0.014 to 0.020 inches and a length that is in the range of about 33 to 60 inches. It should be understood that these dimensions are given only by way of example, and that other dimensions could be used without parting from the spirit and scope of the invention.

For example, in some embodiments, the guidewire can be configured or adapted for use in particular interventions or treatments, and as such, the lengths and diameters of the different sections of the guidewire could be specifically adapted for the particular interventions or treatments being performed.

In some embodiments, the guidewire could be adapted for use in a procedure in which a treatment site, such as a lesion or an occlusion, is relatively close to an access point that provides access to an interior of the vasculature that contains the treatment site. An example of an intravascular treatment in which a treatment site is relatively close to a vascular access point includes Hemodialysis Access Management, or HAM.

Patients who are in End Stage Renal Disease (ESRD) are often given a surgical artificial conduit connecting an artery to a vein for hemodialysis access. This artificial conduit can be native, in which a fistula-surgical connection is made between an artery and a vein, or it can be an artificial graft, in which a prosthetic graft is used to connect an artery to a vein.

In a fistula-surgical connection, the arterial side forces blood at higher pressures through the artificial conduit to the venous side, thereby arterializing the vein. This enlarges the vein so that it can handle the increased arterial blood pressure as well as creating an area for dialysis access. Needles used for dialysis are typically relatively large (often 14 to 16 gauge), so the fistula has to be mature, which can take several weeks to several months.

In a graft, the surgical conduit can be made from a graft such as a 6 millimeter polytetrafluoroethylene (PTFE) graft that connects an artery to a vein. In some cases, the basilic vein (close to the bottom of the elbow) can be used, as this is a common tie in spot for loop grafts. After surgery, the graft can typically be accessed within two or three weeks.

In either case, thrombi can form in the surgical conduit as a result of placement of the conduit (it can bend), changes in blood flow and the like. These thrombi can inhibit blood flow and thus potentially interfere with dialysis. To remove any thrombus that may have formed within the surgical conduit, a sheath such as a 6 French sheath can be used to gain access. Access can be gained to the arterial side and the venous side using the guidewires of the invention. Balloon catheter can be tracked over the guidewires and the balloon can be inflated several times in the thrombosed regions to macerate the thrombus into small pieces.

It is contemplated, however, that the guidewires of the invention can be applicable to other treatments as well, including non-intravascular treatments.

It is to be understood that a broad variety of materials, dimensions and structures can be used to construct suitable embodiments, depending on the desired characteristics. For example, the guidewire can include a central shaft or core wire, one or more sleeves or polymer layers or coatings, one or more coils or springs, for example, spring tips, shaping or safety ribbons or coils, radiopaque markers, and distal tips or caps, or other such structures.

Figure 3:
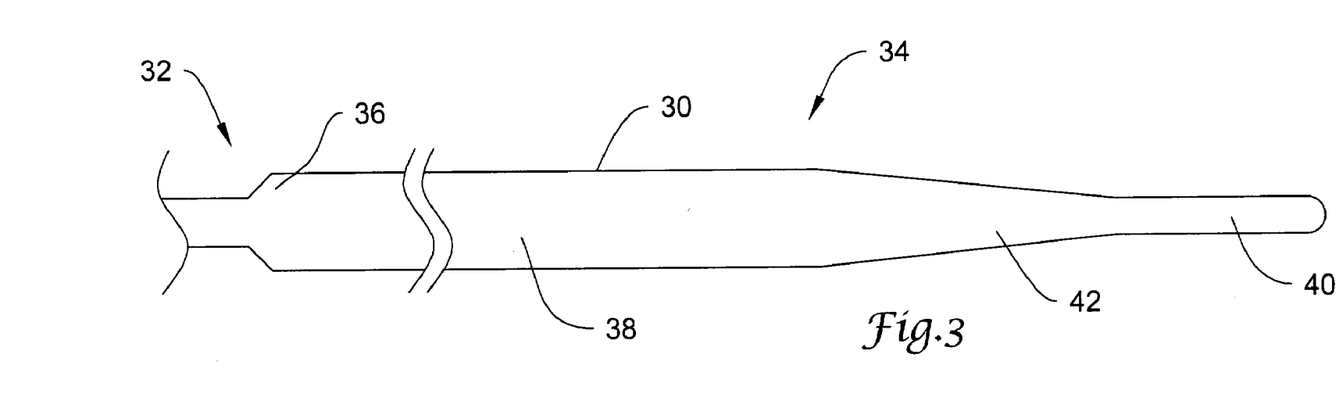
FIG. 3 is a partially sectioned side view of a distal portion of a guidewire core wire in accordance with an embodiment of the invention.

In at least some embodiments, the shape of a core wire can be used to influence or achieve the desired size and shape characteristics of the guidewire. For example, refer now to FIG. 3 illustrates an exemplary core wire 30 that can be used in a guidewire as discussed above. The core wire 30 has a proximal section 32 (partially illustrated) and a distal section 34. As illustrated in FIG. 3, the proximal section 32 includes a relatively constant outer diameter. The distal section 34 can include a proximal constant diameter portion 38 that has a greater outer diameter than the outer diameter of the proximal section 32. The distal section 34 also includes a distal constant diameter portion 40 that has a smaller outer diameter than the outer diameter of the proximal constant diameter portion 38, and an intervening taper portion 42. A transition region 36 separates the proximal section 32 and the distal section 34. In some embodiments, the transition region 36 can be an abrupt transition, with the transition region 36 providing a transition between a diameter of the proximal section 32 and the distal section 34 over a relatively short distance. In some embodiments, the proximal section 32 can have a diameter in the range of about 0.014 to 0.020 inches and a length that is in the range of about 33 to 60 inches. The proximal constant diameter portion 38 can have a diameter that is in the range of about 0.015 to 0.30 inches and a length that is in the range of about 3 to 15 inches. The distal constant diameter portion 40 can have a diameter that is in the range of about 0.002 to 0.006 inches and a length that is in the range of about 0.2 to 0.5 inches. In some embodiments, the taper portion 42 can have an overall length that is in the range of about 2.5 to 10 inches.

As discussed above with regard to the proximal section 20 and the distal section 18 of the guidewire 16, the proximal section 32 and the distal section 34 of a core wire 30 can individually make up a significant portion of the total length of the core wire 30. The core wire 30 can include a similar configuration of proximal section 32 and the distal section 34 as discussed above with regard to the proximal section 20 and the distal section 18 of the guidewire 16. For example, in some embodiments, the distal section 34 of the core wire 30 can make up in the range of about 10% to about 50%, or in the range of about 30% to about 50% of the total length of the guidewire, while the proximal section 32 would make up the remainder.

One of skill will recognize that a guidewire core wire can have a profile different from that illustrated in FIG. 3. For example, proximal section 32 and/or distal section 34, can be continuously tapered, can each have a tapered section or a number or series of tapered sections of differing diameters, or can have a constant diameter. If tapered, the core wire 30 can include a uniform or a non-uniform transition of the sections, depending on the transition characteristics desired. For example, core wire may be linearly tapered, tapered in a curvilinear fashion, or tapered in a step-wise fashion. The angle of any such tapers can vary, depending upon the desired flexibility characteristics. The length of the taper may be selected to obtain a more (longer length) or less (shorter length) gradual transition in stiffness.

In some embodiments, the distal section 34 can be tapered or otherwise formed to have a geometry that decreases in cross sectional area toward the distal end thereof. The structure used to construct the distal section 34 of the core wire can be designed such that a portion, such as the proximal portion 38, is relatively stiff for pushability and torqueability, and a portion, such as distal portion 40 is relatively flexible by comparison for better lateral trackability and steerability.

In some embodiments, the proximal section 32 can have a constant or generally uniform diameter along its length, for example, to enhance usefulness as a guide for other devices. However, embodiments including a proximal section 32 having a tapered portion or a series of tapered portions are also contemplated. The diameter of the proximal section 32 can be sized appropriately for the desired characteristics dependent upon the material used.

The tapered and constant diameter portions along the length of the core wire 30 can be formed by any one of a number of different techniques, for example, by centerless grinding, stamping and the like. A centerless grinding technique can utilize an indexing system employing sensors (e.g., optical/reflective, magnetic) to avoid excessive grinding. In addition, the centerless grinding technique can utilize a CBN or diamond abrasive grinding wheel that is well shaped and dressed to avoid grabbing the core wire 30 during the grinding process.

The core wire 30 can have a solid cross-section as shown, but in some embodiments, can have a hollow cross-section. In yet other embodiments, core wire 30 can include a combination of areas having solid cross-sections and hollow cross sections.

The core wire 30 can be formed of any suitable metallic, polymeric or composite material. In some embodiments, part or all of the core wire 30 can be formed of a metal or a metal alloy. Some examples of suitable metals and metal alloys include stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 825; or the like; or other suitable material. The particular material used can be chosen in part based on the desired characteristics of the core wire 30, for example flexability, pushability, torqueability, and the like.

As indicated above, in some particular embodiments, the core wire 30 can be formed from a superelastic or linear elastic nickel-titanium alloy, for example, linear elastic or superelastic (i.e. pseudoelastic) nitinol. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

Within the family of commercially available nitinol alloys, is a category designated "linear elastic" which, although is similar in chemistry to conventional shape memory and superelastic varieties, exhibits distinct and useful mechanical properties. By skilled applications of cold work, directional stress, and heat treatment, the wire is fabricated in such a way that it does not display a substantial "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range.

For example, in some embodiments, there is no martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy.

In some embodiments, the linear elastic nickel-titanium alloy is in the range of about 50 to about 60 weight percent nickel, with the remainder being essentially titanium. In some particular embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel-titanium alloys include those disclosed in U.S. Pat. Nos. 5,238,004 and 6,508,803, which are incorporated herein by reference.

In at least some embodiments, portions or all of the core wire 30, or other structures included within the medical device may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device in determining its location. Some examples of radiopaque materials can include, but are not limited to, gold, platinum, palladium, tantalum, tungsten alloy, polymer material loaded with a radiopaque filler, and the like.

In some embodiments, a degree of MRI compatibility can be imparted. For example, to enhance compatibility with Magnetic Resonance Imaging (MRI) machines, it may be desirable to make the core wire 30, or other portions of the guidewire, in a manner that would impart a degree of MRI compatibility. For example, the core wire 30, or other portions of the guidewire, may be made of a material that does not substantially distort the image and create substantial artifacts (artifacts are gaps in the image). Certain ferromagnetic materials, for example, may not be suitable because they may create artifacts in an MRI image. Core wire 30, or other portions of the guidewire, may also be made from a material that the MRI machine can image. Some materials that exhibit these characteristics include, for example, tungsten, Elgiloy, MP35N, nitinol, and the like, and others.

The entire core wire 30 can be made of the same material, or in some embodiments, can include portions or sections that are made of different materials. In some embodiments, the material used to construct different portions of the core wire can be chosen to impart varying flexibility and stiffness characteristics to different portions of the wire. For example, a proximal section 32 and a distal section 34 can be formed of different materials (i.e., materials having different moduli of elasticity) resulting in a difference in flexibility. In some embodiments, the material used to construct some portions of the core wire 30 can be relatively stiff for pushability, and the material used to construct other portions of the core wire can be relatively flexible by comparison for better lateral trackability and steerability. For example, the proximal section 32 and the proximal portion 38 of the distal section 34 could be formed of, for example, straightened 304v stainless steel wire, and the distal portion 40 of the distal section 34 can be formed of, for example, a straightened super elastic or linear elastic alloy (e.g., nickel-titanium) wire. In some embodiments, the proximal section 32 can be formed of a relatively flexible material while the distal section 34 is formed of a relatively stiff material.

In embodiments where different portions of the core wire 30 are made of different material, the different portions can be connected using any suitable connecting techniques. For example, the different portions of the core wire 30 can be connected using welding, soldering, brazing, adhesive, or the like, or combinations thereof. Additionally, some embodiments can include one or more mechanical connectors or connector assemblies to connect the different portions of the core wire 30 that are made of different materials. The connector can include any structure generally suitable for connecting portions of a guidewire. One example of a suitable structure includes a structure such as a hypotube or a coiled wire which has an inside diameter sized appropriately to receive and connect the different portions of the core wire 30. Some methods and structures that can be used to interconnect different shaft sections are disclosed in U.S. patent application Ser. Nos. 09/972,276, and 10/086,992, which are incorporated herein by reference. Some additional examples are disclosed in a U.S. patent application Ser. No. 10/375,493 entitled "ARTICULATING INTRACORPORAL MEDICAL DEVICE" filed on even date herewith, which is incorporated herein by reference.

Figure 4:
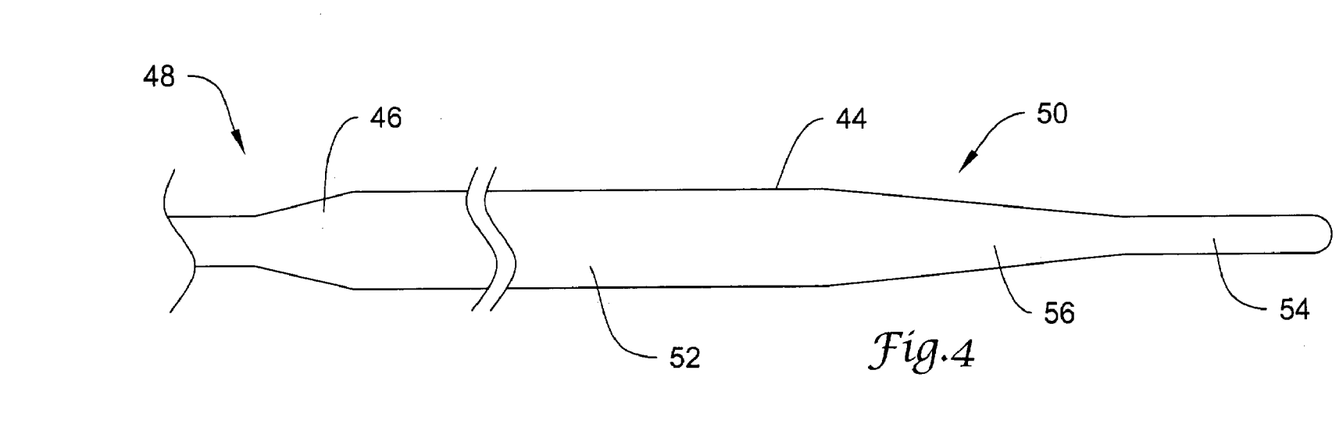
FIG. 4 is a partially sectioned side view of a distal portion of a guidewire core wire in accordance with another embodiment of the invention.
Figure 5:
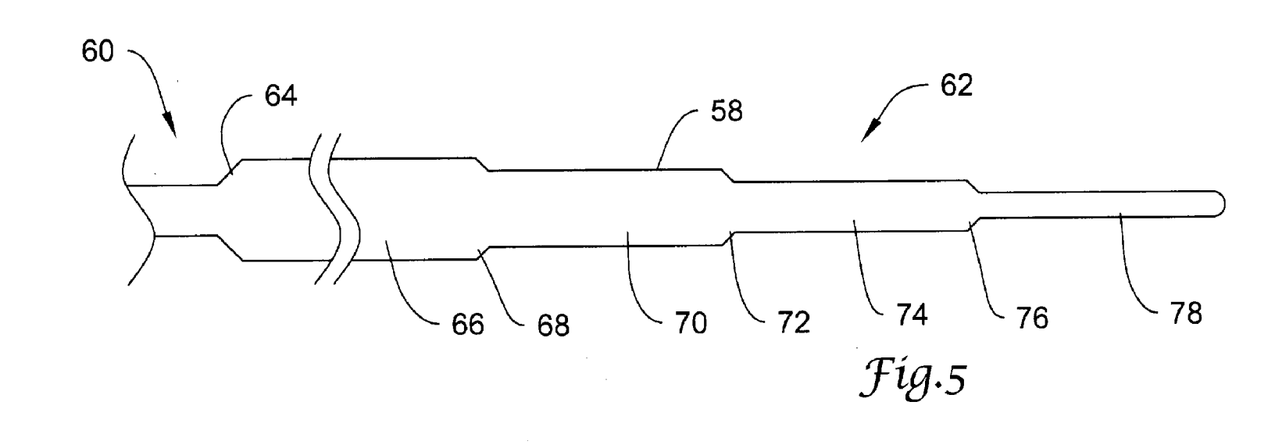
FIG. 5 is a partially sectioned side view of a distal portion of a guidewire core wire in accordance with another embodiment of the invention.
Figure 6:
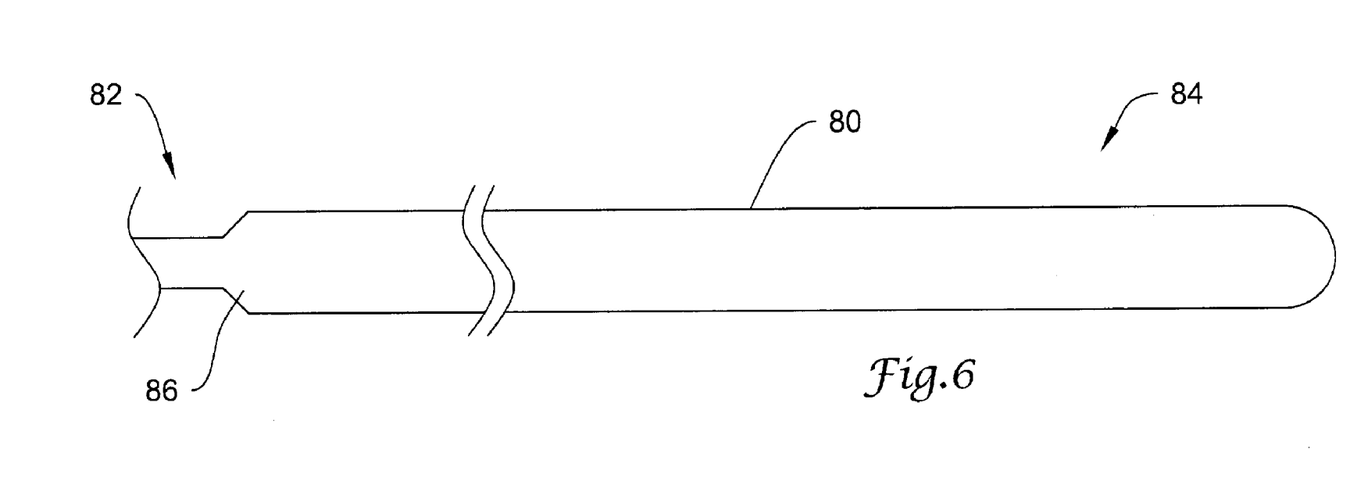
FIG. 6 is a partially sectioned side view of a distal portion of a guidewire core wire in accordance with another embodiment of the invention.

As noted previously, the invention contemplates guidewires having a variety of different distal section profiles. FIGS. 4 through 6 illustrate several additional nonlimiting embodiments.

In FIG. 4, the core wire 44 has a profile that is similar to that of the core wire 30, except that the core wire 44 has a transition region 46 that is more gradual. The transition region 46 can have an overall length that is in the range of about 0.1 to 0.3 inches. The core wire 44 has a proximal section 48 and a distal section 50. The distal section 50 can include a proximal constant diameter portion 52, a distal constant diameter portion 54, and an intervening taper section 56. Each of the proximal section 48 and the distal section 50 can be configured to have the dimensions and properties discussed above with respect to FIG. 3. The core wire 44 can be formed of any suitable metallic or non-metallic material, as discussed above.

FIG. 5 illustrates an embodiment in which a core wire 58 has a proximal section 60, a distal section 62, and an intervening transition region 64. In this embodiment, the distal section 62 can include several constant diameter portions and several taper portions, depending on the particular flexibility parameters desired. As illustrated, the distal section 62 includes, viewing the core wire 58 distally starting at the transition region 64, a first constant diameter portion 66, a first taper portion 68, a second constant diameter portion 70, a second taper portion 72, a third constant diameter portion 74, a third taper portion 76 and a fourth constant diameter portion 78.

Each of these constant diameter portions and taper portions can be dimensioned in accordance with desired flexibility parameters. At least some of the portions of the distal section 62 have an outer diameter that is larger than the outer diameter of the proximal section 60. Each of the proximal section 60, the distal section 62 and the transition region 64 can be configured to have the dimensions and properties discussed above with respect to FIG. 3. The core wire 58 can be formed of any suitable metallic or non-metallic material, as discussed above.

FIG. 6 illustrates another embodiment in which a core wire 80 has a proximal section 82, a distal section 84 and an intervening transition region 86. In this particular embodiment, the distal section 84 of the core wire 80 can have a constant outer diameter that is larger than the outer diameter of the proximal section 82. For example, the distal section 84 can have an illustrative but non-limiting diameter that is in the range of about 0.015 to 0.03 inches while the proximal section can have an illustrative but non-limiting diameter that is in the range of about 0.01 to 0.02 inches. The core wire 80 can be formed of any suitable metallic or non-metallic material, as discussed above.

The previous FIGS. 3-6 have illustrated exemplary but non-limiting examples of core wire configurations. As illustrated in FIGS. 7-10, guidewires can include structures and elements in addition to the core wire, such as coils, atraumatic tips and various sleeves and coatings, and the like.

Figure 7:
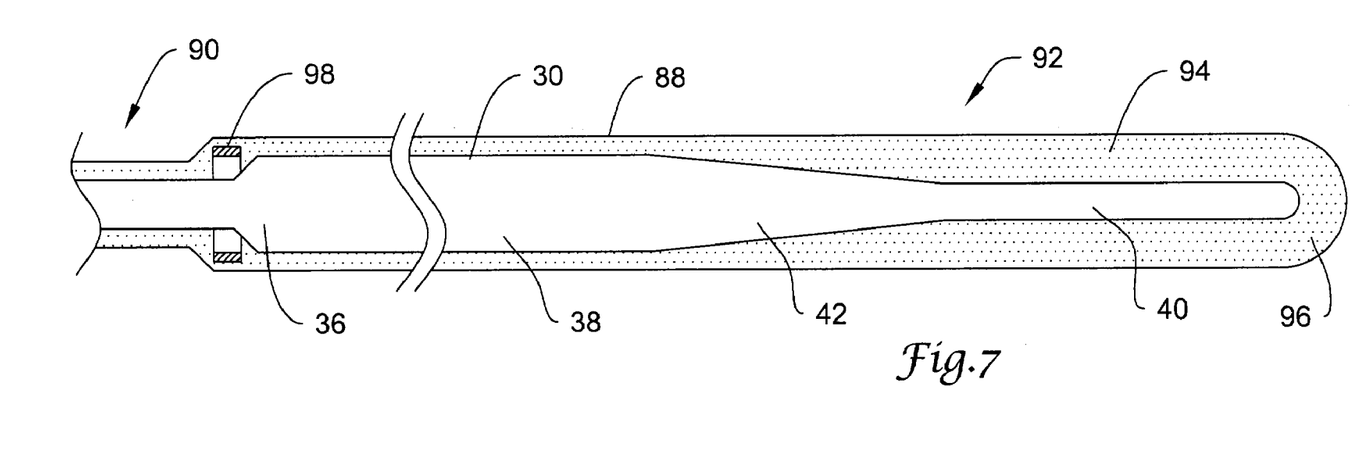
FIG. 7 is a partially sectioned side view of a distal portion of a guidewire employing the core wire of FIG. 3.
Figure 8:
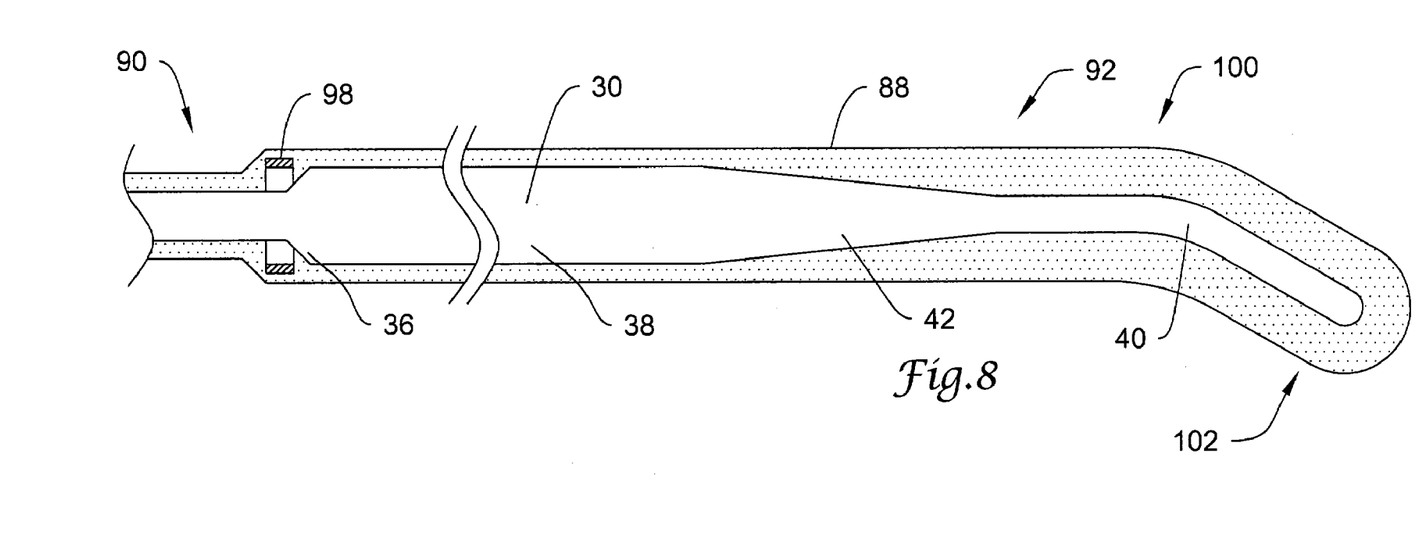
FIG. 8 is a partially sectioned side view of the distal portion of a guidewire of FIG. 7, shown in an alternate configuration.

FIG. 7 illustrates a guidewire 88 that has a core wire 30 that has a proximal section 90, a distal section 92 and an intervening transition region 36. The core wire 30 can be manufactured according to the structure and materials discussed above, for example, with respect to FIG. 3. In this embodiment, one or more layer or sleeve 94 is disposed over the core wire 30. As illustrated, the core wire 30 is encased within the sleeve 94, and the sleeve can form an atraumatic tip 96.

The sleeve 94 can have a first, smaller outer diameter over the proximal section 90 and a second, larger outer diameter over the distal section 92. In some embodiments, the sleeve 94 can have a first constant outer diameter that is in the range of about 0.012 to 0.02 inches over the proximal section 90 and a second constant outer diameter that is in the range of about 0.025 to 0.04 inches over the distal section 92.

The use of a sleeve can serve several functions, such as improving the flexibility properties of the guidewire. Choice of materials for the sleeve 94 will vary the flexibility. For example, polymers with a low durometer or hardness will make a very flexible or floppy tip. Conversely, polymers with a high durometer will make a tip which is stiffer. The use of certain materials for the sleeve can also provide a more atraumatic tip for the guidewire. An atraumatic tip is better suited for passing through fragile body passages. Finally, a sleeve can act as a binder for radiopaque materials, as discussed in more detail below.

The sleeve 94 can be made from any material that can provide the desired strength, flexibility or other desired characteristics. For example, the sleeve can be made of a polymer, or other like material. Some examples of suitable polymer material include any of a broad variety of polymers generally known for use as guidewire polymer sleeves. In some embodiments, the polymer material used is a thermoplastic polymer material. Some examples of some suitable materials include polyurethane, elastomeric polyamides, block polyamide/ethers (such as Pebax), silicones, and co-polymers. The sleeve may be a single polymer, multiple layers, or a blend of polymers.

The sleeve 94 can be made from several different suitable materials such as several different polymers. For example, the sleeve 94 can be formed from several polymer segments (not illustrated) that can be joined together using any suitable technique such as adhesives or applying heat and pressure. Each polymer segment can be formed of different polymers having different hardness values, or of polymers bearing differing levels of radiopaque materials.

By employing careful selection of materials and processing techniques, thermoplastic, solvent soluble, and thermosetting variants of these materials can be employed to achieve the desired results.

Further examples of suitable polymeric materials include but are not limited to poly(L-lactide) (PLLA), poly(D,L-lactide) (PLA), polyglycolide (PGA), poly(L-lactide-co-D, L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), poly D,L-lactide-co-caprolactone) (PLA/PCL), poly(glycolide-co-caprolactone) (PGA/PCL), polyanhydrides (PAN), poly(ortho esters), poly(phosphate ester), poly (amino acid), poly(hydroxy butyrate), polyacrylate, polyacrylamid, poly(hydroxyethyl methacrylate), polyurethane, polysiloxane and their copolymers, and the like.

In some embodiments, the sleeve 94, or portions thereof, can include, or be doped with, radiopaque material to make the sleeve 94, or portions thereof, more visible when using certain imaging techniques, for example, fluoroscopy techniques. Any suitable radiopaque material known in the art can be used. Some examples include precious metals, tungsten, barium subcarbonate powder, and the like, and mixtures thereof. In some embodiments, the sleeve 94 can include different sections having different amounts of loading with radiopaque material. For example, the sleeve 94 can include a distal section having a higher level of radiopaque material loading, and a proximal section having a correspondingly lower level of loading.

The sleeve 94 can be disposed around and attached to the core wire 30 using any suitable technique for the particular material used. In some embodiments, the sleeve 94 can be attached by heating a sleeve of polymer material to a temperature until it is reformed around the core wire 30. In some other embodiments, the sleeve 94 can be attached using heat shrinking or adhesive techniques. In some other embodiments, the sleeve 94 can be attached by co-extruding the sleeve 94 with the core wire 30. The sleeve 94 can be finished, for example, by a centerless grinding or other method, to provide the desired diameter and to provide a desired outer surface texture.

In some embodiments, it is also contemplated that a separate radiopaque member or a series of radiopaque members, such as radiopaque coils, bands, tubes, or other such structures could be attached to the guidewire core wire 30, or incorporated into the core wire by plating, drawing, forging, or ion implantation techniques. In particular embodiments, a radiopaque member 98 can be positioned proximate the transition region 36.

In some embodiments, the distal section 92 can be at least substantially linear. In some embodiments, as illustrated for example in FIG. 8, the distal end 100 of the guidewire 88 can include an angled distal tip 102. The angled distal tip 102 can be formed in any suitable manner and can be angled at any useful angle that might be beneficial in steering the guidewire 88 through various portions of a patient's vasculature or other anatomy.

Figure 9:
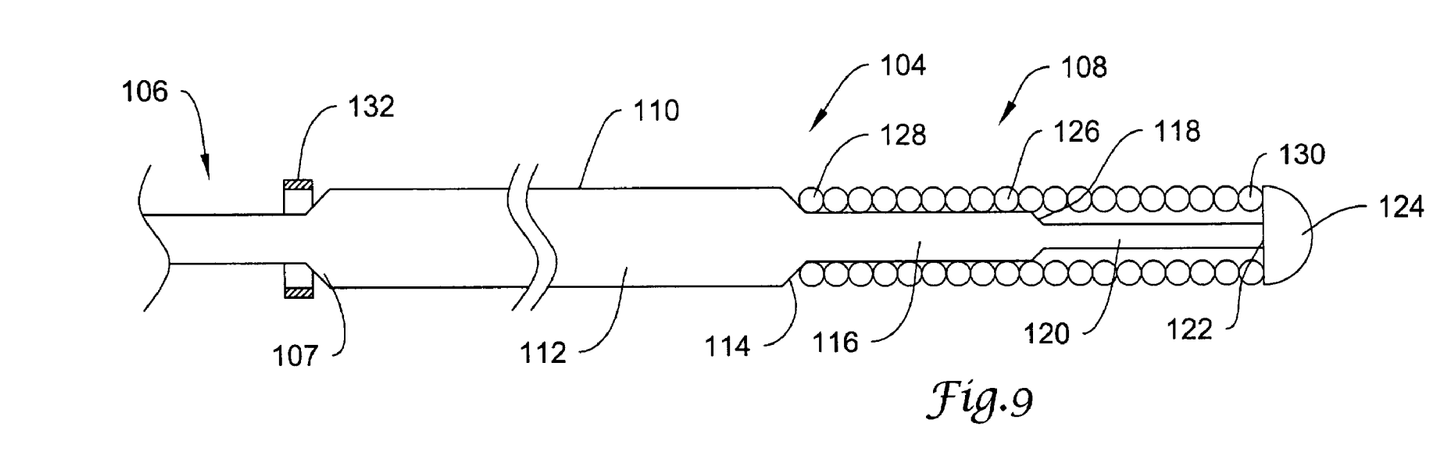
FIG. 9 is a partially sectioned side view of a distal portion of a guidewire in accordance with another embodiment of the invention.
Figure 10:
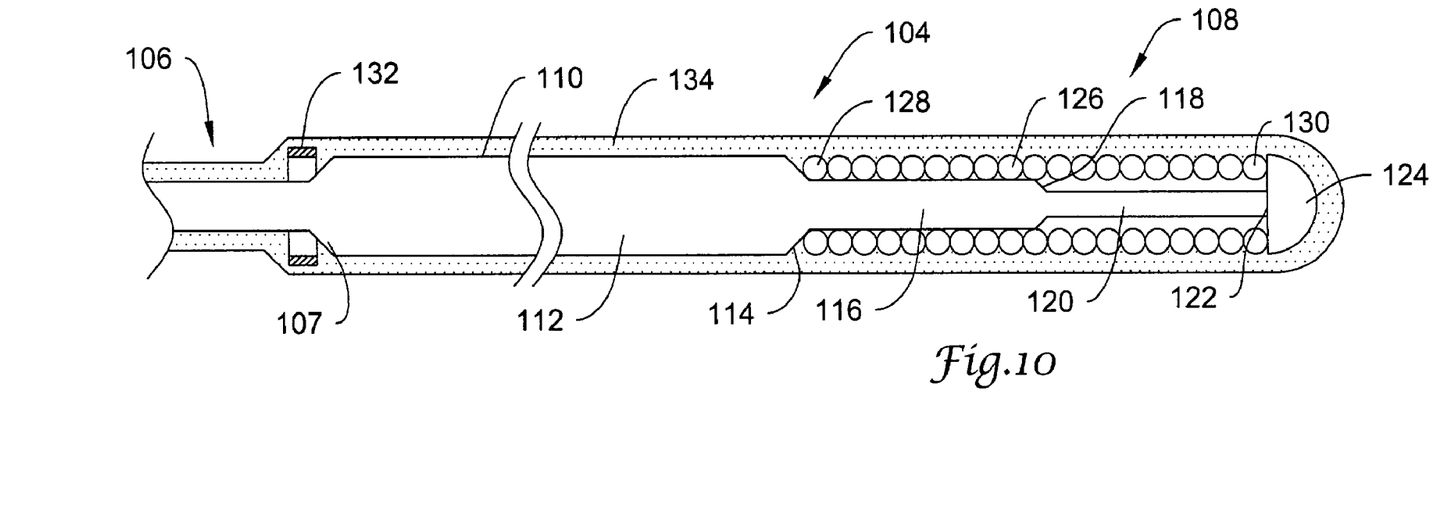
FIG. 10 is a partially sectioned side view of the distal portion of a guidewire of FIG. 9, shown in an alternate configuration.

FIGS. 9 and 10 illustrate example embodiments in which a guidewire 104 includes a spring or coil type tip design. The guidewire 104 includes a core wire 110 that has a proximal section 106, a distal section 108, and an intervening transition region 107. The core wire 110 can be formed using the materials and dimensions discussed previously with respect to FIG. 3. As illustrated, the distal section 108 can include a proximal constant diameter portion 112, an intermediate constant diameter portion 116, and a distal constant diameter portion 120. At least the proximal constant diameter portion 112 has an outer diameter that is larger than the outer diameter of the proximal section 106 of the core wire 110. A proximal taper portion 114 can be positioned between the distal and intermediate portions 112, 116 and a distal taper portion 118 can be positioned between the intermediate and distal constant diameter portions 116, 120. The distal section 108 can be configured such that each constant diameter portion 112, 116 and 120, and each taper portion 114, 118 are dimensioned in accordance with desired flexibility properties.

As illustrated, the guidewire 104 can include a coil 126 disposed over at least a portion of the distal section 108. In this embodiment, a proximal end 128 of the coil 126 is positioned adjacent the proximal taper portion 114 and a distal end 130 of the coil 126 is positioned proximate an atraumatic tip 130, for example, a solder tip, weld tip, polymer tip, prefabricated tip, or the like, as is generally known. In other embodiments (not illustrated), the coil 126 could be positioned such that its proximal end 128 is positioned distally of the proximal taper portion 114. In some embodiments, the coil 126 can include one or more additional coils (not illustrated).

The coil 126 can be formed of a variety of materials including metals, metal alloys, polymers, and the like. Some examples of material for use in the coil include those discussed above with regard to the core wire. For example, in some embodiments, it can be advantageous for the coil 126 to include radiopaque materials, as discussed above with respect to the core wire 30. Additionally, in some embodiments, it may be desirable that the coil be imparted with a degree of MRI compatibility, as discussed above with respect to the core wire 30.

The coil 126 can be formed of round or flat ribbon ranging in dimensions to achieve desired characteristics, such as flexibility. In some embodiments, the coil 126 can be a round ribbon in the range of about 0.001-0.015 inches in diameter, and can have a length in the range of about 0.1 to about 20 inches, however, other dimensions are contemplated. The coil 126 can be wrapped in a helical fashion by conventional winding techniques. The pitch of adjacent turns of the coil 126 may be tightly wrapped so that each turn touches the succeeding turn or the pitch may be set such that the coil 126 is wrapped in an open fashion.

As indicated in FIG. 10, in some embodiments, the guidewire 104 can include a sleeve 134, for example a polymer sleeve, that is disposed over the coil 126 and/or some or all other portions of the guidewire. The polymer sleeve 134 can be manufactured and attached using any suitable materials and methods, as outlined above with respect to FIG. 7. For example, the polymer sleeve 134 can extend over just the proximal section 106, just the distal section 108, or can extend over substantially the entire length of the guidewire 104. As illustrated, in some embodiments the polymer sleeve 134 can have a first, smaller outer diameter over the proximal section 106 and a second, larger outer diameter over the distal section.

A guidewire in accordance with some embodiments of the invention can optionally include a coating layer such as a lubricious coating layer over part or all of the guidewire.

Hydrophobic coatings such as fluoropolymers provide a dry lubricity which improves guide wire handling and device exchanges. Lubricious coatings improve steerability and improve lesion crossing capability. For example, in some embodiments it can be useful but not necessary for the proximal section 106 (see FIG. 10) to include a lubricious coating.

Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. In some embodiments, the more distal portion of the guidewire is coated with a hydrophilic polymer as discussed above, and the more proximal portions is coated with a fluoropolymer, such as polytetrafluroethylene (PTFE).

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

I claim:

1. A guidewire for use in an anatomy of a patient, the guidewire comprising:
    a core wire that extends from a position adjacent a distal end of the guidewire to a position adjacent a proximal end of the guidewire, the core wire having a distal section and a proximal section;
    the distal section including a portion having an outside diameter that is greater than an outside diameter of the proximal section;
    the distal section having a length configured to extend from a first position adjacent a target site in the anatomy to a second position outside the patient during use;
    wherein the proximal section is 50% or more of a total length of the guidewire;
    wherein the distal section of the core wire has a length that is in the range of about 6 to about 18 inches; wherein the proximal section is more flexible than the distal section.

2. The guidewire of claim 1, wherein the proximal section has a length configured to extend from the first position adjacent the target site in the anatomy to the second position outside the patient.

3. The guidewire of claim 1, wherein 20% or more of the distal section has an outside diameter that is greater than the outside diameter of the proximal section.

4. The guidewire of claim 1, wherein 50% or more of the distal section has an outside diameter that is greater than the outside diameter of the proximal section.

5. The guidewire of claim 1, wherein the outer diameter of the proximal section is substantially constant along the length thereof.

6. The guidewire of claim 1, wherein the distal section of the core wire includes a proximal portion and a distal portion, and the proximal portion has an outside diameter that is greater than the outside diameter of the proximal section of the core wire.

7. The guidewire of claim 1, wherein the distal section comprises one or more constant diameter portions and one or more tapered portions.

8. The guidewire of claim 1, wherein the proximal section comprises one or more constant diameter portions and one or more tapered portions.

9. The guidewire of claim 1, wherein the target site in the anatomy is accessible through a blood vessel in the anatomy, and the distal section has a length configured to extend from the target site, through the blood vessel and to the second position outside the patient.

10. The guidewire of claim 1, wherein the target site in the anatomy is accessible through a blood vessel in the anatomy, and the proximal section has a length configured to extend from the target site, through the blood vessel and to the second position outside the patient.

11. The guidewire of claim 1, wherein the proximal section of the core wire has a length that is in the range of about 33 to 60 inches.

12. The guidewire of claim 5, wherein the proximal section of the core wire has a diameter in the range of about 0.014 to about 0.02 inches.

13. The guidewire of claim 1, further comprising a polymer sleeve disposed about at least a portion of the core wire.

14. The guidewire of claim 1, further comprising a coil disposed about at least a portion of the distal section of the core wire.

15. The guidewire of claim 1, further comprising a radiopaque marker member disposed adjacent a junction between the distal section and the proximal section of the core wire.

16. A method of accessing a treatment site within an anatomy of a patient, the method comprising:
    providing a guidewire including an elongate shaft having a proximal section and a distal section, the distal section including a portion having an outside diameter that is greater than an outside diameter of the proximal section and a length configured to extend from a first position adjacent a target site within the anatomy to a second position outside the patient, and the proximal section also having a length configured to extend from the first position adjacent the target site within the anatomy of the patient to the second position outside the patient wherein the proximal section is more flexible than the distal section;
    inserting the distal section through an access point in the anatomy of the patient;
    advancing the distal section within the anatomy until the distal section extends from the first position adjacent the target site within the anatomy to the second position outside the patient; and
    advancing the proximal section within the anatomy until the proximal section extends from the first position adjacent the target site within the anatomy to the second position outside the patient, wherein the distal section is advanced distally of the treatment site within the anatomy.

17. The method of claim 16, further comprising advancing an intervention device over the proximal section of the guidewire.

18. The method of claim 17, wherein the intervention device comprises a balloon catheter, an infusion catheter, a stent deployment catheter, or a cutting balloon catheter.

* * * * *